United States Patent [19]

Pommier et al.

[11] Patent Number: 4,904,258
[45] Date of Patent: Feb. 27, 1990

[54] BIOCOMPATIBLE, HYDROPHILIC MATERIAL, METHOD OF MANUFACTURE AND USES OF SAME

[75] Inventors: Jean-Claude Pommier, Gradignan; Joel Poustis, Pessac; Charles Baquey, St Medard en Jalles; Dominique Chauveaux, Bordeaux, all of France

[73] Assignees: La Cellulose Du Pin; Universite de Bordeaux II, both of Bordeaux, France

[21] Appl. No.: 74,047

[22] Filed: Jul. 16, 1987

[30] Foreign Application Priority Data

Jul. 16, 1986 [FR] France ................... 86 10331

[51] Int. Cl.$^4$ ............................. A61F 2/28; C08B 9/00
[52] U.S. Cl. ........................................ 623/16; 623/66; 623/901; 536/60
[58] Field of Search ................. 536/60, 124, 127, 128; 428/221; 623/16

[56] References Cited

U.S. PATENT DOCUMENTS

| | | | |
|---|---|---|---|
| 3,108,357 | 10/1963 | Liebig et al. | 623/1 |
| 4,210,747 | 7/1980 | Sorsa et al. | 536/60 |
| 4,270,914 | 6/1981 | Dahl | 536/60 |
| 4,284,765 | 8/1981 | Geyer, Jr. et al. | 536/60 |
| 4,287,334 | 9/1981 | Fauth et al. | 536/60 |
| 4,289,875 | 9/1981 | Geyer et al. | 536/60 |
| 4,342,600 | 8/1982 | Mayer et al. | 536/60 |
| 4,468,428 | 8/1984 | Early et al. | 428/221 |

FOREIGN PATENT DOCUMENTS

| | | |
|---|---|---|
| 1310496 | 10/1962 | France . |
| 2147139 | 9/1973 | France . |
| 86/01113 | 2/1986 | World Int. Prop. O. . |

OTHER PUBLICATIONS

Gazette Van Antwerpen, Nov. 8, 1977, p. 7; "Houtenbeen": Le tissu osseux respousse dans les pores de diverses sortes de bois notamment le bois de frene ou de bouleau.

Primary Examiner—Richard J. Apley
Assistant Examiner—David J. Isabella
Attorney, Agent, or Firm—Oblon, Spivak, McClelland, Maier & Neustadt

[57] ABSTRACT

A biocompatible hydrophilic material is based on purified cellulose, from which material all or the majority of the water has been removed and which has a modulable potential for water recovery of up to an amount of water of approximately 60%. The material can be used for the production of fitting sheaths for articulated prostheses.

11 Claims, 1 Drawing Sheet

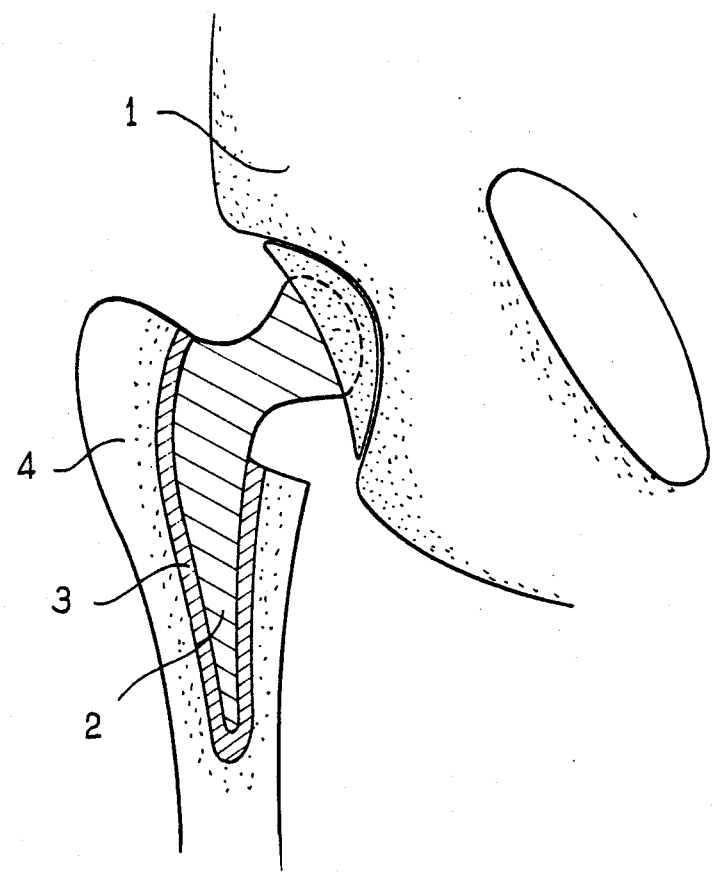

BIOCOMPATIBLE, HYDROPHILIC MATERIAL, METHOD OF MANUFACTURE AND USES OF SAME

BACKGROUND OF THE INVENTION

1. Field of the Invention

The present invention relates to a biocompatible hydrophilic material, its method of manufacture and its uses, in particular in the human body.

2. Background of the Prior Art

Faced with a lack of bone due to pathological or traumatic causes, which, if permanent, can have biomechanical or even esthetic consequences, the doctor is obliged to intervene in an attempt to promote the reconstitution of the missing bone or to make up for this lack by practicing a bone graft or by fixing a suitably selected biomaterial.

Practice of an auto-graft is one solution, but the usable sources (ribs, hipbones, spongy epiphysary bones) are limited with regard to the amounts available and their use is not always compatible with the patients' state of health. Lacking an autograft, the surgeon can practice a homo-graft if he has a well-administered and well-stocked bank close by. Nevertheless, the quantitative availability remains limited.

Therefore, the availability of bone mass substitutes of an allogenic origin clearly appears as the only solution capable of flexibly and effectively meeting the needs. The materials proposed for the manufacture of such substitutes are generally composites which contain a naturally-originating mineral phase, such as coral, or, most frequently, of synthetic origin, such as hydroxyapatite, tricalcium phosphate and an organic phase acting as a binder and which assists cellular colonization by the adjacent receiving tissues.

Numerous studies carried out on the subject for the most part show the suitability of such composite mixtures for the filling of losses of bone substance, but the proposed methods for preparation and use thereof are not fully satisfactory. In addition, the cost of the starting materials prevents their use for filling the large-sized cavities encountered in traumatology or carcinology.

Another field of use for a biocompatible material is the field of articulated prostheses.

The prostheses presently produced in a metallic or synthesized material can be sealed to the bone by a binder such as an acrylic cement. One of the disadvantages of this type of sealing is the atrophy of the adjacent living cells due to the temperature of polymerization of the cement.

In accordance with one alternative, the prostheses can also be sealed by biological anchoring. In this case, a bone regrowth is promoted which, should the prosthesis need to be removed, for example if it were to break, complicates its removal.

SUMMARY OF THE INVENTION

The invention proposes reversible sealing which overcomes the cited disadvantages. The sealing in accordance with the invention uses a biocompatible material having a potential for volume expansion which is capable of creating normal stresses at opposite surfaces, which are opposed to the relative movements of the prosthetic part and the prosthesized bone. The material in accordance with the invention placed between the prosthesis element and the receiving part of the bone provides a "modulable stress joint" sealing. When the above-identified potential is released, the resulting expansion is accompanied by a degradation of the mechanical properties of the material, which facilitates the removal of the prosthesis.

One of the objects of the invention is a biocompatible hydrophilic material which has properties enabling its use, in particular, for the restoration of skeletal defects or as an adjuvant in the placing of articulated prostheses.

A material conforming to the invention is a material based on purified cellulose, from which, by drying, all or the majority of the water has been removed, and which has a potential for water recovery which is modulable up to a water content of approximately 60%.

This material is obtained in particular as a result of the following operations:

alkali-cellulose is prepared by steeping cellulose pulp, and particularly the pulp obtained by the method of pulping cellulose in a liquor of bisulfite acid in a sodium hydroxide solution followed by drying and pressing to achieve a weight of dry cellulose of between 30 and 40%, the alkali-cellulose is then sulfurated using carbon sulfide, preferably in excess in relation to the stoichiometric quantities, in order to obtain sodium xanthate, the sodium xanthate is dissolved in a diluted sodium hydroxide solution to obtain viscose, that is, a solution containing cellulose and sodium hydroxide in well-determined proportions, preferably 7 to 12% by weight of cellulose and 4 to 8% by weight of sodium hydroxide, the viscous solution obtained is submitted to heat treatment so as to provoke the coagulation of the viscose and to treatment for removal of the sulfur, so as to obtain an amorphous material with rubber-like characteristics, and the material obtained is dried.

DETAILED DESCRIPTION OF THE INVENTION

In accordance with one embodiment of the method, the coagulation of the viscose solution is first provoked by a heat treatment, for example by bringing said solution to approximately 100° C. for approximately 1–2 hours, then the sulfur is eliminated by washing with water and with a product which is reactive to sulfur, such as sodium sulfite or sodium carbonate, with the washing consisting of several successive washings. In order to increase the efficacy of the washing, a heating or treatment of the coagulated block in the washing bath can preferably be provided by microwaves.

In an alternative method, the sulfur removal treatment is carried out at least partially before carrying out the coagulation using a heat treatment.

In a preferred embodiment, the sulfur removal phases and the coagulation phases are alternated.

In effect, it has been noted that too great a coagulation of the viscose solution rendered difficult the subsequent sulfur removal. On the other hand, too great a sulfur removal prior to coagulation also rendered difficult the coagulation. Therefore, it is preferred to carry out a partial sulfur removal by treating the viscose solution with a agent which reacts with the sulfur, such as sodium sulfite and sodium carbonate, for example in an amount of approximately 10 g of sodium sulfite and 2 g of sodium carbonate for 100 cm$^3$ of viscose solution. Then the coagulation is commenced. It is washed with water and this sequence of operations is possibly repeated.

This method enables amounts of sulfur of less than 0.1% by weight of the weight of the material to be achieved.

In accordance with one characteristic of the method, the drying is carried out by hot pressing of the material obtained after coagulation of the cellulose. For this purpose, the material can be placed in a drying chamber at a temperature of approximately 100° C. and under a pressure of approximately 1 to 10 bars for approximately 24 hours.

The material obtained can be easily machined to obtain parts of all shapes. In effect, this material has mechanical properties close to those of wood and it can be machined in a similar or even better manner since, unlike wood, this material is isotropic.

This highly hydrophilic material is capable of water recovery equivalent to approximately 60% of its weight for an approximately 90% increase in volume and, in such case, loses all mechanical holding characteristics. However, when the expansion volume available is nil or is limited, the absorption of water is necessarily moderated, going up to approximately 20% by weight and the loss of mechanical properties remains acceptable for the applications envisaged.

In one of the preferred embodiments of the invention, reinforcing fibers, in particular papermaking fibers, are incorporated into the material during its preparation and preferably before the cellulose coagulation operation. The amount of incorporated fibers which are found in the material obtained can vary from 0 to 50% by weight in relation to the overall weight of the composite material. The incorporation of the above-identified fibers improves certain characteristics of the material, in particular the stress resistance.

One of the particularly advantageous applications of this material in accordance with the invention, which exploits its previously mentioned properties, is the manufacture of a fitting sheath for articulated prostheses, in particular for the ends of hip prostheses which enable reversible anchoring in the medullar canal of the femur.

The material is sufficiently biocompatible to cause no lesions nor necroses on the living tissues with which it must be interfaced.

Another quality of the material is that it enables an adjustment which is resistant to movements by the end of the hip prosthesis in the medullar canal of the femur, on the one hand, in rotation and, on the other hand, in axial translation. Due to its water recovery potential, the material recovers the water provided in a determined amount during sealing. Through the related volume expansion, forces of pressure are established which oppose the relative movements of the prosthesis and the receiving bone part.

Due to its properties and in particular its water recovery potential, the material also permits reversible placing of prostheses and eliminates the disadvantages of cement-sealed or self-sealing prostheses whose removal is particularly delicate, in particular in the case of breakage of the prosthesis. Thus, for the removal of a prosthesis in accordance with the invention, it is sufficient to artificially provide a supplement of water to the cover which will then lose its properties of mechanical resistance.

An alternative embodiment for preparation of the hydrophilic material enables parts with multiple shapes to be obtained directly. This alternative consists of molding the material obtained after coagulation of the cellulose while extracting the water and taking into account the shrinkages corresponding to the removal of the majority of the water.

Another application of the hydrophilic material in accordance with the invention is its use in the restoration of skeletal defects. In accordance with one characteristic of the invention, the limiting surface of the material can be modified chemically such that the cells of the receiving tissue can colonize it in a controlled manner. The cytocompatibility of the material can also be modulated or improved by radiochemical cross-linking and/or grafting.

Other advantages and characteristics of the invention will become apparent from the examples described below.

EXAMPLE 1

This example describes the preparation of the porous material capable of being used in particular to produce fitting sheaths for ends of prostheses.

650 g of cellulose pulp were treated using a solution of 6M sodium hydroxide in accordance with the reaction.

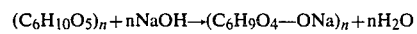

$$(C_6H_{10}O_5)_n + nNaOH \rightarrow (C_6H_9O_4-ONa)_n + nH_2O$$

In this manner impurities such as residual hemi-celluloses and resins were removed and alkali-cellulose was formed. The cellulose/NaOH ratio was controlled by pressing the suspension until a weight of dry cellulose of approximately 35% was obtained and by removing part of the excess sodium hydroxide and dissolved hemi-celluloses.

The xanthate was then prepared by sulfuration of the alkali-cellulose using carbon sulfide, $CS_2$, in a reactor by using the $CS_2$ in an amount of 31% by weight of the weight of the cellulose, in accordance with the reaction

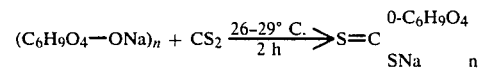

$$(C_6H_9O_4-ONa)_n + CS_2 \xrightarrow[2\ h]{26-29°\ C.} S=C\begin{matrix} O-C_6H_9O_4 \\ SNa \end{matrix}_n$$

The xanthate was then dissolved in a solution of diluted sodium hydroxide. At the end of the operation, the solution contained an amount of cellulose of approximately 9% and approximately 5% of sodium hydroxide. The viscose obtained was deaerated. The solution was heated at 100° C. for 2 hours which caused coagulation. It was then washed several times with water, sulfite and sodium carbonate. A compact, amorphous and relatively rubbery material was obtained. This material was then pressed for 24 hours at a temperature of 110° C. under a pressure of 2 bars, which removed the water it contained.

A material was obtained which had the appearance of natural wood.

This hydrophilic material obtained could be used in accordance with the invention for various applications. Its mechanical properties, such as rigidity in bending, compression and tension were comparable to those of natural wood. This isotropic material could be machined easily.

From the hydrophilic material obtained, a fitting sheath was machined for a metallic end of a hip prosthesis in order to apply the concept of sealing with a joint having modulable stress.

A model assembly was produced composed of a section of a human origin femoral diaphysis, the canal of which was fitted with the metallic part constituting the end of the prosthesis, enveloped by the machined sheath of the porous material. One of the advantages of the material used is that the ratio of occupation of the canal by the sheath can easily be adjusted and that the resistance of the assembly can be optimized.

The assembly was immersed in physiological serum at 37° C. The prevention of the volume expansion was translated by the establishment of normal pressures at the interface limiting the expansion.

FIG. 1 shows very diagrammatically the articulation of the hip 1 with the prosthesis end 2 enveloped by the machined sheath 3 of the hydrophilic material in accordance with the invention in place in the medullar canal of the femur 4.

The assembly is resistant to the static stresses of longitudinal and rotational shearing. The sheath also contributes to the absorption of numerous dynamic influences with which the articulated prosthesis is confronted.

The modulus of elasticity of the hydrophilic material is measured as between 7 and 12 gigapascals whereas that of a conventional methyl polymethacrylate cement is between 5.1 and 5.7 gigapascals. The material in accordance with the invention is less rigid and more shock-absorbent.

EXAMPLE 2

The method of Example 1 was repeated, except that paper-making reinforcing fibers in an amount of approximately 30% by weight of the viscose were incorporated into the viscose solution prior to the coagulation operation.

The product obtained was able to be machined as easily as the hydrophilic product prepared in accordance with Example 1.

Stress resistance was improved.

EXAMPLE 3

The method of Example 1 was repeated, except that the viscose was subjected to a treatment for partial removal of the sulfur prior to the coagulation operation. For this purpose, sodium sulfite and sodium carbonate in amounts of 10 g of sodium sulfite and 2 g of sodium carbonate for 100 cm$^3$ of viscose solution were added to the viscose solution. This was stirred at room temperature. The coagulation was then commenced by heating the solution at 100° C. for approximately 1 hour. The block obtained was washed several times with hot water and with cold water.

After drying, a material which had the appearance of natural wood was obtained, the sulfur content of which was approximately 0.9%.

What is claimed as new and desired to be secured by Letters Patent of the United States is:

1. A method for the manufacture of a biocompatible hydrophilic material based on purified cellulose, from which material the majority of the water has been removed by drying, and which has a modulable potential for water recovery of up to an amount of water of approximately 60%, comprising the following steps:
   a. preparing alkali-cellulose by steeping cellulose pulp using bisulfite acid in a sodium hydroxide solution followed by drying and pressing to achieve a weight of dry cellulose of between 30 and 40%,
   b. then sulfurating the alkali-cellulose using carbon sulfide at least in stoichiometric quantities, in order to obtain sodium xanthate,
   c. dissolving the sodium xanthate in a diluted sodium hydroxide solution to obtain a viscose solution containing cellulose and sodium hydroxide in well-determined proportions,
   d. submitting the viscose obtained to heat treatment so as to provoke the coagulation of the viscose and to treatment for removal of the sulfur, so as to obtain an amorphous material with rubber-like characteristics,
   e. and drying the material obtained.

2. The method in accordance with claim 1, wherein the coagulation of the cellulose is first provoked by a heat treatment and the sulfur is then removed by washing, with water and a product which is reactive with the sulfur.

3. The method of claim 2, wherein said sulfur-reactive product is sodium sulfite, sodium carbonate or both.

4. The method in accordance with claim 2, wherein the removal of sulfur by washing is carried out in the presence of microwave heating.

5. The method in accordance with claim 1, wherein the sulfur is partially removed from the viscose solution by treatment with a product which is reactive with the sulfur, prior to provoking the coagulation.

6. The method in accordance with claim 5, wherein the sulfur removal phases by treatment with a product which is reactive with the sulfur, and washing with water are alternated with the coagulation phases.

7. The method in accordance with claim 1, wherein the water is removed by heat pressing.

8. The method in accordance with claim 1, wherein the water is removed in a mold so as to directly obtain a product having the desired shape.

9. The method in accordance with claim 1, wherein reinforcing fibers are incorporated in the viscose solution.

10. The method of claim 1, wherein in step b. a stoichiometric excess of carbon disulfide is used, and the viscose obtained in step c. comprises 7–12% by weight of cellulose and 4–8% by weight of sodium hydroxide.

11. The method of claim 2, wherein the removal of sulfur by washing with water and a product which is reactive with sulfur are repeated several times.

* * * * *